(12) United States Patent
Pang et al.

(10) Patent No.: US 11,400,183 B2
(45) Date of Patent: Aug. 2, 2022

(54) THREE DIMENSIONAL MICROTISSUE BIOPRINTER

(71) Applicant: The General Hospital Corporation, Boston, MA (US)

(72) Inventors: Yonggang Pang, Boston, MA (US); Brian Grottkau, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 210 days.

(21) Appl. No.: 15/757,461

(22) PCT Filed: Sep. 2, 2016

(86) PCT No.: PCT/US2016/050167
§ 371 (c)(1),
(2) Date: Mar. 5, 2018

(87) PCT Pub. No.: WO2017/040975
PCT Pub. Date: Mar. 9, 2017

(65) Prior Publication Data
US 2018/0243478 A1  Aug. 30, 2018

Related U.S. Application Data

(60) Provisional application No. 62/214,551, filed on Sep. 4, 2015.

(51) Int. Cl.
*B29C 67/00* (2017.01)
*A61L 27/38* (2006.01)
(Continued)

(52) U.S. Cl.
CPC ....... *A61L 27/3834* (2013.01); *A61L 27/3804* (2013.01); *A61L 27/3847* (2013.01);
(Continued)

(58) Field of Classification Search
CPC ......... B33Y 10/00; B33Y 30/00; B33Y 50/00; B33Y 50/02; A61L 27/3834;
(Continued)

(56) References Cited

U.S. PATENT DOCUMENTS

| 7,033,761 B2 | 4/2006 | Shafer |
| 7,051,654 B2 | 5/2006 | Boland et al. |

(Continued)

FOREIGN PATENT DOCUMENTS

| WO | 0174490 A2 | 10/2001 |
| WO | 2004007204 A2 | 1/2004 |

(Continued)

OTHER PUBLICATIONS

Faulkner-Jones, et al., Development of a Valve-Based Cell Printer for the Formation of Human Embryonic Stem Dell Spheroid Aggregates, Biofabrication, 2013, 5(1):015013, 12 pages.

(Continued)

*Primary Examiner* — Ryan M Ochylski
(74) *Attorney, Agent, or Firm* — Quarles and Brady LLP

(57) ABSTRACT

A bioprinter comprises one or more dispensing units. Each dispensing unit may include (i) a syringe including a hollow body and a plunger dimensioned to translate in the body wherein the body has an exit orifice; (ii) an actuator in contact with a proximal end of the plunger; (iii) a controller for moving the actuator; and (iv) a nozzle having a wall defining a fluid path extending from an inlet of the nozzle to an outlet of the nozzle. The inlet of the nozzle is in fluid communication with the exit orifice of the syringe body. The nozzle includes a fluid passageway in fluid communication with a source of fluid and the fluid path. The bioprinter can be used in a method of preparing microtissue comprising dispensing a bioink from one or more dispensing units of the (Continued)

bioprinter on a plate. The microtissue may comprise cartilage cells or tumor cells or liver cells.

14 Claims, 12 Drawing Sheets

(51) Int. Cl.

| | | |
|---|---|---|
| B41J 2/04 | (2006.01) | |
| A61L 27/50 | (2006.01) | |
| C12M 1/26 | (2006.01) | |
| B01L 3/02 | (2006.01) | |
| B29C 64/112 | (2017.01) | |
| C12N 5/071 | (2010.01) | |
| B29C 64/209 | (2017.01) | |
| B33Y 10/00 | (2015.01) | |
| B33Y 30/00 | (2015.01) | |
| B33Y 50/02 | (2015.01) | |
| G01N 33/50 | (2006.01) | |

(52) U.S. Cl.
CPC ........... *A61L 27/3852* (2013.01); *A61L 27/50* (2013.01); *B01L 3/0268* (2013.01); *B29C 64/112* (2017.08); *B29C 64/209* (2017.08); *B33Y 10/00* (2014.12); *B33Y 30/00* (2014.12); *B33Y 50/02* (2014.12); *B41J 2/04* (2013.01); *C12M 33/00* (2013.01); *C12N 5/0671* (2013.01); *C12N 5/0697* (2013.01); *G01N 33/5011* (2013.01); *A61L 2400/06* (2013.01); *A61L 2430/02* (2013.01); *A61L 2430/06* (2013.01); *B01L 2200/0673* (2013.01); *B01L 2300/1822* (2013.01); *B01L 2400/0478* (2013.01); *B01L 2400/0487* (2013.01)

(58) Field of Classification Search
CPC ........... A61L 27/3847; A61L 27/3852; G01N 33/5011; B29C 64/112
See application file for complete search history.

(56) References Cited

U.S. PATENT DOCUMENTS

| | | |
|---|---|---|
| 7,857,756 B2 | 12/2010 | Warren et al. |
| 8,636,938 B2 | 1/2014 | Bonassar et al. |
| 2009/0263849 A1 | 10/2009 | Sun et al. |
| 2010/0166969 A1 | 7/2010 | Batchelder |
| 2012/0089238 A1* | 4/2012 | Kang ................... B29C 64/112 623/23.72 |
| 2012/0288938 A1 | 11/2012 | Forgacs et al. |
| 2013/0017564 A1 | 1/2013 | Guillemot et al. |
| 2014/0070462 A1* | 3/2014 | Kraibuhler ........... B29C 64/209 264/401 |
| 2014/0354731 A1 | 12/2014 | Masuda |
| 2015/0037445 A1 | 2/2015 | Murphy et al. |
| 2015/0343673 A1* | 12/2015 | Williams ................ B29C 39/12 264/1.37 |
| 2016/0325498 A1* | 11/2016 | Gelbart ................ B22D 23/003 |
| 2016/0367358 A1* | 12/2016 | Tran ........................ C08L 89/06 |

FOREIGN PATENT DOCUMENTS

| | | |
|---|---|---|
| WO | 2006005923 A1 | 1/2006 |
| WO | 2015066705 A1 | 5/2015 |
| WO | 2015107333 A1 | 7/2015 |

OTHER PUBLICATIONS

Moon, et al., Layer By Layer Three-Dimensional Tissue Epitaxy by Cell-Laden Hydrogel Droplets, Tissue Engineering: Part C, 2010, 16(1):157-166.

Steadman, et al., PolyHEMA Spheroids are an Inadequate Model for the Drug Resistance of the Intractable Solid Tumors, Cell Cycle, 2008 7(6):818-829.

European Patent Office, Extended European Search Report, Application No. 16843097.3, dated May 14, 2019, 9 pages.

International Search Report and Written Opinion for International Application No. PCT/US2016/050167 dated Nov. 28, 2016, 7 pages.

Machine Translation of CN 104403923A.

* cited by examiner

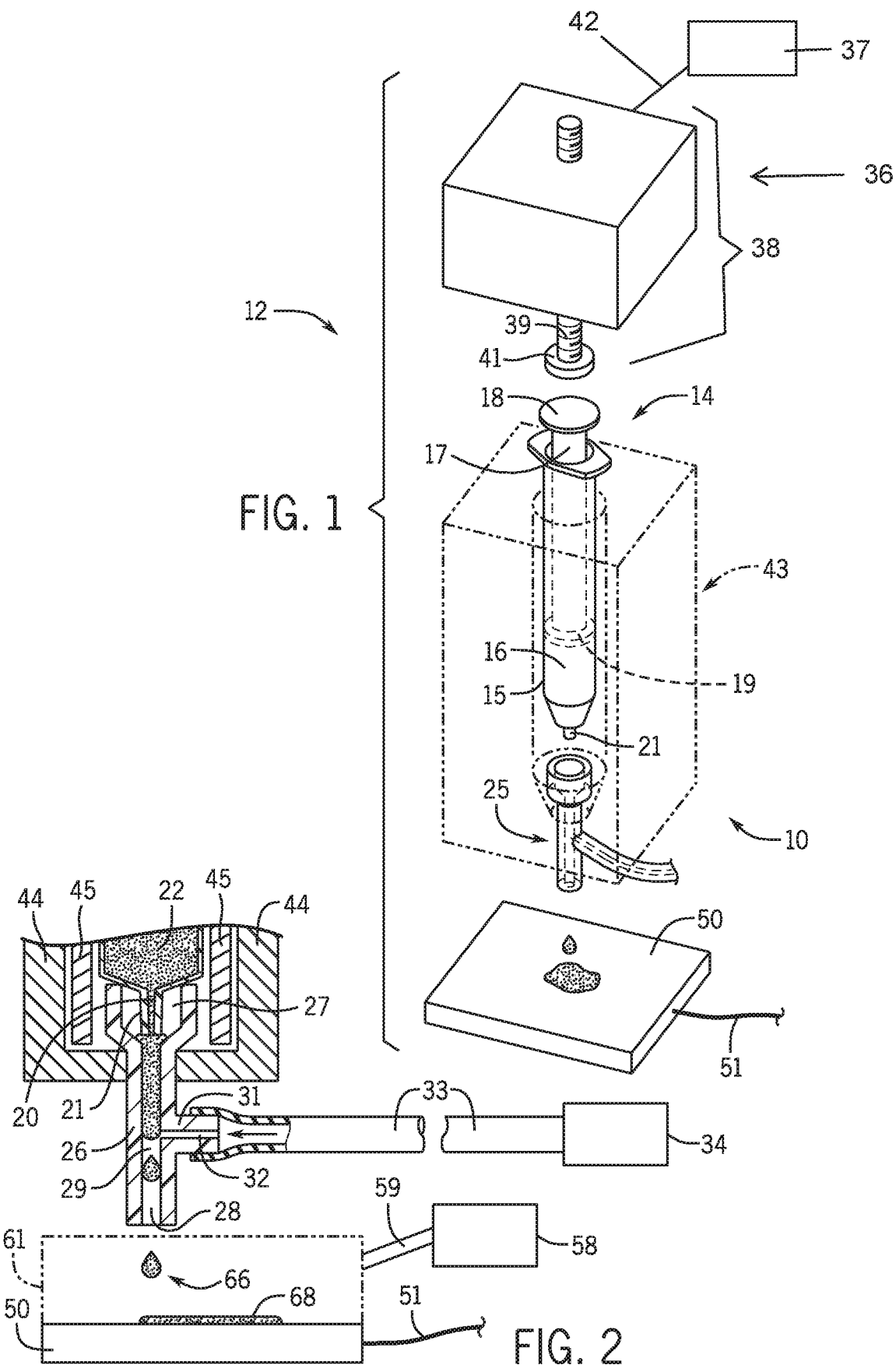

THREE DIMENSIONAL MICROTISSUE BIOPRINTER

CROSS-REFERENCE TO RELATED APPLICATIONS

This application is a U.S. National Phase of PCT Application No. PCT/US2016/050167 filed on Sep. 2, 2016 which claims priority from U.S. Patent Application No. 62/214,551 filed Sep. 4, 2015.

STATEMENT REGARDING FEDERALLY SPONSORED RESEARCH

Not Applicable.

BACKGROUND OF THE INVENTION

1. Field of the Invention

The invention relates to three-dimensional bioprinting, and more particularly to a computer controlled programmable three dimensional (3D) bioprinter generating live microtissues with precisely controlled microscale accurate XYZ motion and volumetric nanoliter dispensing capability.

2. Description of the Related Art

Bioprinters were developed to try and meet the challenge of printing three dimensional tissues. Bioprinters fabricate structures via a dropwise printing of cells with a material which serves as the "bio-glue". Bioprinters are limited by slow throughput inherent in the small size of their building materials as well as the vast number of building units that must be deposited. Various techniques and technologies exist for various applications of bioprinting.

Contact bioprinting is polymer printing without cells, and is used by the 3D Bioplotter available from the Envisiontec company. The polymer printing method only prints a scaffold with a plastics-like polymer.

Live cell bioprinting uses contact live cell bioprinting in bulk sizes. This technique does not allow microtissue printing as the resultant tissues are a couple of centimeters in size. Contact live cell bioprinting can only perform low throughput printing.

Non-contact valve based bioprinting techniques provide cell only bioprinting. See, for example, Faulkner-Jones, et al., "Development of a valve-based cell printer for the formation of human embryonic stem cell spheroid aggregates", *Biofabrication* 5.1 (2013): 015013. Non-contact valve based bioprinting techniques can also provide cell and hydrogel bioprinting. See, for example, Moon, et al., "Layer by layer three-dimensional tissue epitaxy by cell-laden hydrogel droplets", *Tissue Engineering* Part C: Methods 16.1 (2009): 157-166. Moon, et al. printed the droplets into a larger piece and their system could only generate a structure with cells suspended in the hydrogel without tissue architecture or morphology. Other commercial printers are unable to print tissue with architecture and morphology similar to native tissues.

Air driven dispensing can provide coaxial gas flow bead generation. This technique uses continuous air flow and continuous dispensing material flow in a coaxial setup, which cannot control the volume of each droplet and cannot dispense a single droplet. This technique ordinarily dispenses thousands of droplets at a time, and in commercial systems, such as those available from Nisco Engineering AG, the material is limited to alginate.

In cell aggregates-non-real 3D models, cell aggregates are generated by a hanging-drop-method or from a non-adherent cell culture surface. This technique has been used by others trying to mimic 3D tissue and there are commercial products available. However, the aggregates are just piled two dimensional cells without extracellular matrix. For example, it has been shown that the drug resistance mechanism of cell aggregates is the same as two dimensional confluent cells. See, for example, Steadman, Kenneth, et al. "PolyHEMA spheroids are an inadequate model for the drug resistance of the intractable solid tumors." *Cell Cycle* 7.6 (2008): 818-829. Also, two dimensional cell culture does not resemble the complex biological or pathological nature in vivo. Animal models do not fully resemble human diseases because of species differences.

From the clinical perspective, minimally invasive approaches are always preferred for joint and many bone surgeries. Others have injected chondrocytes taken from the knee and mesenchymal stem cells in the hopes of repairing tissue defects. However, weak mechanical properties, volume shrinkage and long time in vivo growth make it inapplicable to joint cartilage or bone repair.

Therefore, there exists a need for a technology for printing human tissues in vitro that resemble the nature of human tissues in vivo.

SUMMARY OF THE INVENTION

In one aspect, the present disclosure provides a bioprinter comprising one or more dispensing units. Each dispensing unit may include (i) a syringe including a hollow body and a plunger dimensioned to translate in the body wherein the body has an exit orifice; (ii) an actuator in contact with a proximal end of the plunger; (iii) a controller for moving the actuator; and (iv) a nozzle having a wall defining a fluid path extending from an inlet of the nozzle to an outlet of the nozzle. The inlet of the nozzle is in fluid communication with the exit orifice of the body of the syringe. The nozzle includes a fluid passageway in fluid communication with a source of fluid and the fluid path. The bioprinter can be used in a method of preparing microtissue comprising dispensing a bioink from one or more dispensing units of the bioprinter on a plate. The microtissue may comprise stem cells, bone cells, cartilage cells, liver cells, tumor cells, tumor stromal cells, endothelial cells, and other types of cells. The bioprinter can be used in a method for repairing a bone defect or a cartilage defect comprising dispensing bioink from one or more dispensing units of the bioprinter to create microtissue comprising cartilage cells; and implanting the microtissue in a bone defect or a cartilage defect. The bioprinter can be used in a method for high-throughput screening for drug discovery comprising dispensing bioink from one or more dispensing units of the bioprinter to create a plurality of microtissue samples; and contacting at least a portion of the plurality of microtissue samples with a drug candidate compound. The microtissue samples may comprise tumor cells.

In this aspect, the controller may execute a program received from a computer in the controller to drive the actuator toward the proximal end of the plunger to dispense a bioink from the body of the syringe. The bioprinter may further comprise a temperature controller surrounding the body of the syringe, a temperature controlled plate for receiving a bioink from the outlet of the nozzle, and a humidifier for creating a humidity controlled zone adjacent to the temperature controlled plate. In the bioprinter, fluid from the fluid passageway can separate droplets of dispensed material and may force the droplets of dispensed material to exit the outlet of the nozzle. In the bioprinter, a volume of each droplet may be in a range of 10 nanoliters to 15 microliters. The source of fluid may comprise a controllable value for supplying fluid. The controllable value may be controlled by a second controller. The source of fluid in the bioprinter may comprise a controllable valve for supplying pulsed fluid, pulsed air, millisecond pulsed air and sub-millisecond pulsed air. In the bioprinter, each dispensing unit may be a non-contact dispensing unit, the nozzle may be integral with the syringe body, and the nozzle may be separate from the syringe body. The outlet of the nozzle can have an inner diameter of 100 microns to 3 millimeters. The bioprinter may comprise a plurality of dispensing units, and each of the dispensing units may be mounted on an XYZ motion system.

In another aspect, the present disclosure provides a bioprinter comprising one or more dispensing units. Each dispensing unit includes (i) a syringe including a hollow body and a plunger dimensioned to translate in the body, wherein the body has an exit orifice; (ii) an actuator in contact with and moving a proximal end of the plunger; (iii) a controller for controlling the motion of the actuator; and (iv) a nozzle having a wall defining a fluid path extending from an inlet of the nozzle to an outlet of the nozzle. The inlet of the nozzle is in fluid communication with the exit orifice of the body of the syringe. The syringe does not include a valve between the exit orifice of the body of the syringe and proximal end of the plunger. The bioprinter can be used in a method of preparing microtissue comprising dispensing a bioink from one or more dispensing units of the bioprinter on a plate. The microtissue may comprise stem cells, bone cells, cartilage cells, liver cells, tumor cells and other types of cells. The bioprinter can be used in a method for repairing a bone or cartilage defect comprising dispensing bioink from one or more dispensing units of the bioprinter to create microtissue comprising cartilage cells; and implanting the microtissues in a bone or cartilage defect. The bioprinter can be used in a method for high-throughput screening for drug discovery comprising dispensing bioink from one or more dispensing units of the bioprinter to create a plurality of microtissue samples; and contacting at least a portion of the plurality of microtissue samples with a drug library to find candidate compounds. The microtissue samples may comprise tumor cells.

In this version of the bioprinter, the controller may execute a program stored in the controller to drive the actuator toward the proximal end of the plunger to dispense a bioink from the body of the syringe. The bioprinter may further comprise a temperature controller surrounding the body of the syringe, a temperature controlled plate for receiving a bioink from the outlet of the nozzle, and a humidifier for creating a humidity controlled zone adjacent to the temperature controlled plate. The nozzle in the bioprinter may include a fluid passageway in fluid communication with a source of fluid and the fluid path. The fluid from the fluid passageway may separate droplets of dispensed material and may force the droplets of dispensed material to exit the outlet of the nozzle. In the bioprinter, a volume of each droplet may be in a range of 10 nanoliters to 15 microliters. The source of fluid may comprise a controllable value for supplying fluid. The controllable value may be controlled by a second controller. The source of fluid in the bioprinter may comprise a controllable valve for supplying pulsed fluid, pulsed air, millisecond pulsed air and sub-millisecond pulsed air. In the bioprinter, each dispensing unit may be a non-contact dispensing unit, the nozzle may be integral with the syringe body, and the nozzle may be separate from the syringe body. The outlet of the nozzle can have an inner diameter of 100 microns to 3 millimeters. The bioprinter may comprise a plurality of dispensing units, and each of the dispensing units is mounted on an XYZ motion system.

One version of the bioprinter of the present disclosure is a computer controlled programmable 3D bioprinter generating live micro tissues with precisely controlled micro-scale accurate XYZ motion and volumetric nanoliter dispensing capability.

One version of the bioprinter of the present disclosure directly prints human cells and extra cellular matrix mixtures onto the surface of cell culture containers, such as culture dishes and micro plates. The printed tissues have the morphology and function of native tissues. The bioprinter works in two modes: (1) high speed printing mode which is used to bioprint micro tissues in large amount for the purpose of tissue regeneration; and (2) precision print mode, which bioprints one, or a specific number of, microtissue(s) into each well of a 96 or 384 well plate for drug screening and personalized therapeutic purposes.

Our bioprinter has a computer controlled XYZ linear motion system, which controls the position and the movement of the aligned dispensing units (e.g., printing heads). Each dispensing unit dispenses our tissue of interest including cells or matrix or a specified mixture of the two (bio-ink) using the following mechanism. The dispensing unit is composed of: (1) a linear actuator-driven syringe pump controlled by a computer, (2) a dispensing syringe, which holds the bio-ink and dispenses a pre-determined nanoliter-volume material through the nozzle each time; and (3) a novel dispensing nozzle. Because an adhesion force exists between the nozzle and the dispensed material, without external force, only larger droplets, about 50 microliters and above, can be generated by gravity force alone. We use a millisecond pulse air dispensing unit to blow the nanoliter level dispensed material away from the syringe nozzle and dispense it onto the surface. The short pulse air flow has very accurate positioning and does not interfere with the already dispensed droplets.

The printed tissues are in high throughput format for drug screening. The bioprinter rapidly prints live and functional micro tissues for tissue regeneration and modeling. The printed tissues can be composed of: (1) primary type of cells, such as tumor cells, hepatocytes and cardiomyocytes, (2) supporting cells, and (3) extracellular matrix so that they function as native tissues because the micro environment of the tissues are reconstructed. Additionally, we can bioprint stem cells with matrix for cartilage and bone regeneration. We theorize that we can bioprint fibroblasts capable of producing elastin, a molecule that diminishes through life resulting in wrinkles. This could have a profound impact on cosmetic surgery. The ability to print a variety of other tissues is limitless.

The volumetric non-contact dispensing unit is superior to existing dispensing technology. The volumetric dispensing unit extrudes cells and/or matrix mixture out of the dispensing nozzle at nanoliter resolution; the extrusion is accomplished via a linear actuator. Because the extruded cell-matrix mixture cannot fall off the nozzle by gravity when the volume is at nanoliter level, our dispensing unit uses millisecond air pulses to blow it away from the nozzle to accomplish the dispensing. Other non-contact printer heads, which are valve-based or piezoelectric, rely on timing or pressure to control the volume of dispensing. They need calibration for different viscosity materials while ours does not.

We are able to print micro tissues with morphology similar to the native tissue. In order to accomplish this, we print the droplets of bioink onto a temperature controlled surface to partially solidify the printed bio-ink during printing and control humidity to keep the printed bioink from drying and to maintain high cell viability. Our precise technology allows us to print tissue systems morphologically comparable to native tissues.

Our system can use a coaxial setup or a non-coaxial setup for delivery of pulsed air. A non-coaxial setup has better position control of the dispensed material.

Our results show that our printed tumor micro tissues, with the same components as native tumor tissue, are much more drug resistant to chemotherapy drugs than the cell aggregates. Additionally, there are many types of cells that do not aggregate and are not amenable to conventional cell aggregating techniques. We can still print these non-aggregating tissues using our bioprinter/technique. This represents a much more realistic testing scenario.

Our bioprinted microtissue is predeveloped and mechanically enhanced in vitro. Once injected in vivo, the tissues self-assemble into large tissue amalgamations which can repair the defects.

Our bioprinted microtissue fills a need in predicting drug effectiveness or other medication on the human organism.

These and other features, aspects, and advantages of the present invention will become better understood upon consideration of the following detailed description, drawings, and appended claims.

BRIEF DESCRIPTION OF THE DRAWINGS

FIG. 1 is a perspective view of a bioprinter according to the invention with a partially exploded section showing the dispensing unit of the bioprinter.

FIG. 2 is a partial side view, with the dispensing unit in cross-section, of the bioprinter of FIG. 1.

DETAILED DESCRIPTION OF THE INVENTION

Figure 2A:
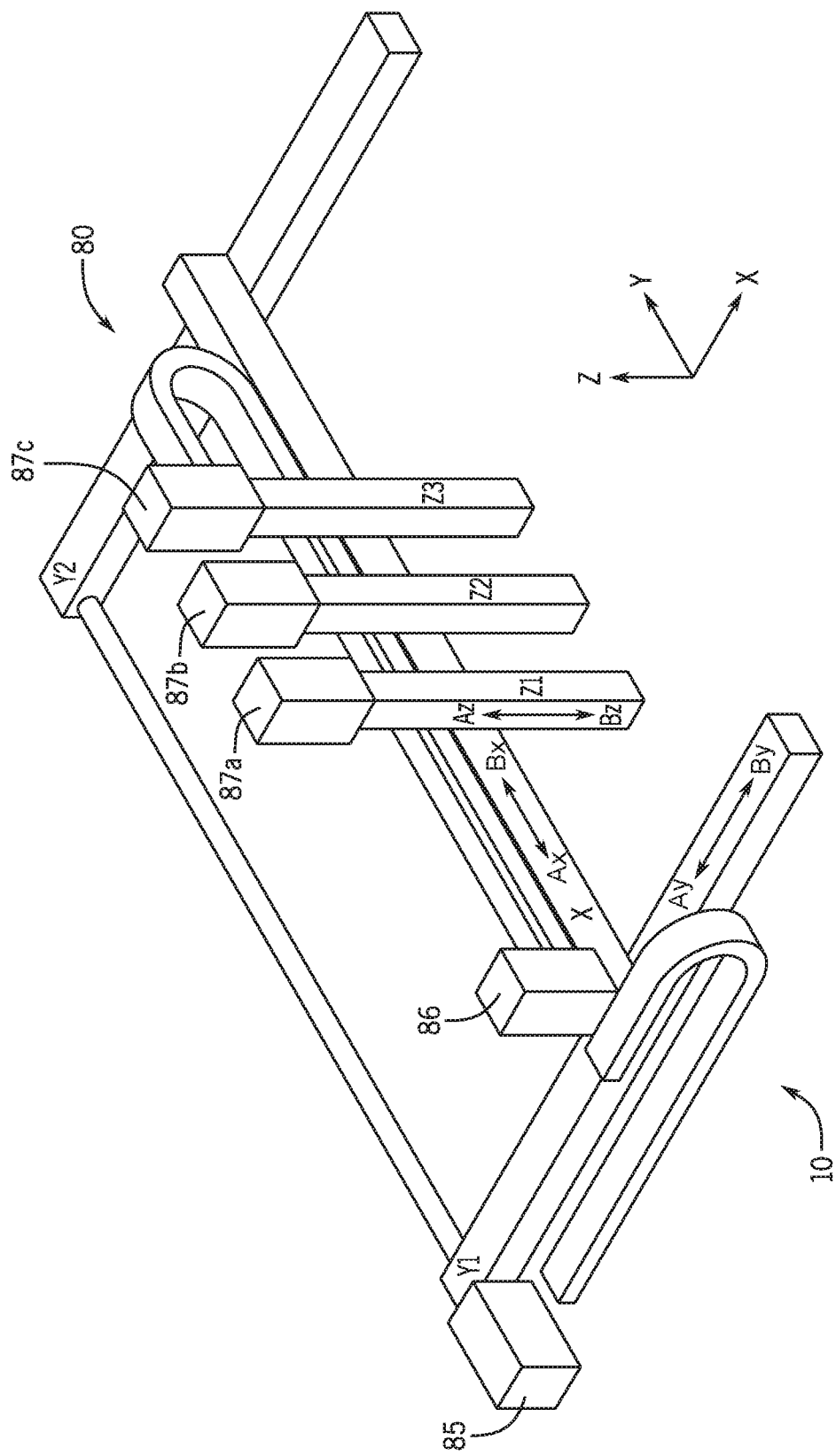
FIG. 2A is a perspective view of the XYZ motion system of the bioprinter of FIGS. 1 and 2.

Referring now to FIGS. 1 and 2, there is shown one non-limiting example embodiment of a bioprinter 10 according to the invention. The bioprinter 10 may include a plurality of dispensing units 12. For ease of illustration and description, one dispensing unit 12 is shown in FIG. 1. The dispensing unit 12 includes a syringe 14, a nozzle 25, an actuation mechanism 36, and a temperature controller 43 (shown in dashed lines in FIG. 1).

The syringe 14 has a body 15 defining a hollow interior space 16 of the syringe 14. Typically, the body 15 comprises an opaque, translucent, or transparent polymeric material, such as polypropylene. A plunger 17 having a disk-shaped proximal end 18 and a disk-shaped distal end 19 is positioned in the interior space 16 of the syringe 14 for movement toward and away from an exit orifice 20 defined by a dispensing tip 21 of the syringe 14. A bioink 22 is contained in the interior space 16 of the syringe 14. No valve is required between the exit orifice 20 of the body 15 of the syringe 14 and the distal end 19 of the plunger.

The nozzle 25 has a side wall 26, an inlet 27, and an outlet 28, which may have an inside diameter of 100 microns to 3 millimeters. The side wall 26 defines a fluid path 29 in the nozzle 25 between the inlet 27 and the outlet 28. The nozzle 25 includes a fluid port 31 that defines a fluid passageway 32 in fluid communication with the fluid path 29 in the nozzle 25. A fluid conduit 33 places the fluid passageway 32 of the fluid port 31 in fluid communication with a source of fluid 34. A controllable valve can be placed between the fluid conduit 33 and the source of fluid 34 for supplying fluid to the fluid passageway 32 of the fluid port 31. The controllable valve can be controlled by a controller that opens and closes the controllable valve to deliver pulsed fluid (e.g., air) from the source of fluid 34 to the fluid passageway 32 of the fluid port 31. In the version of the dispensing unit 12 shown, the nozzle 25 is separate from the body 15 of the syringe 14. However, the nozzle 25 can be integral with the body 15 of the syringe 14.

The actuation mechanism 36 of the dispensing unit 12 includes a controller 37 and an actuator 38 having a leadscrew 39 and a disk shaped distal end section 41. The controller 37 may be linked to the actuator 38 through an electrical cable 42. When the syringe 14 is installed in the dispensing unit 12, the distal end section 41 of the actuator 38 is placed in contact with the proximal end 18 of the plunger 17. The actuator 38 is a linear actuator. The actuator 38 is a step motor based device. Through the leadscrew 39 and rotating locker mechanism inside, the actuator 38 converts the rotation of a step motor inside the actuator 38 into the linear motion of the leadscrew 39. The distance which the distal end 41 travels depends on the degree of step motor rotation. The degree of rotation is controlled by the controller 37 which receives the command sent from a computer program. The leadscrew 39 moves toward the proximal end 18 of the plunger 17 to dispense the bioink 22 from the body 15 of the syringe 14.

The temperature controller 43 of the dispensing unit 12 includes a housing 44 that surrounds temperature controlling elements 45, such as Peltier cooling-and-heating elements. The temperature controller 43 provides a temperature controlled enclosure to surround the syringe 14 and dispensing nozzle 25. One purpose of the temperature controlled enclosure is to control the temperature of the bioink 22 (e.g., cells and/or matrix) at a desired level, which is cold most of time and may be warmed occasionally according to different applications.

Still referring to FIGS. 1 and 2, the bioprinter 10 includes a temperature control plate 50 for receiving bioink 22 that is dispensed from the dispensing unit 12. The temperature control plate 50 may comprise resistive heating elements or Peltier cooling-and-heating elements. that receive electricity via an electrical lead 51. The bioprinter 10 also includes a humidifier 58 with a tubular flow director 59. The humidifier 58 creates a humidity controlled zone 61 adjacent the temperature control plate 50. Droplets 66 of the bioink 22 exit outlet 28 of the nozzle 25 and create microtissue 68 on the temperature control plate 50.

Looking at FIG. 2A, the bioprinter 10 includes an XYZ motion system 80 having a support X, a support $Y_1$, a support $Y_2$, and housings Z1, Z2, Z3, which each house a dispensing unit 12 as shown in FIG. 1. A drive control mechanism 85 controls motion of support $Y_1$, and support $Y_2$ towards and away from each other in directions Ay and By shown in FIG. 2. A drive control mechanism 86 controls motion of support X in directions Ax and Bx shown in FIG. 2. A drive control mechanisms 87a, 87b, 87c control motion of housings Z1, Z2, Z3 in directions Az and Bz shown in FIG. 2. The drive control mechanisms 85, 86, 87a, 87b, 87c may be in electrical communication with a programmable controller for controlling XYZ motion of the housings Z1, Z2, Z3 (which each house a dispensing unit 12). Each dispensing unit 12 is mounted to a Z-axis.

In FIG. 2A, three Z axis dispensing unit housings Z1, Z2, Z3 are shown as a non-limiting representative number. However, there is no limitation on the number of dispensing units; it depends on how many components are needed to print for a specific microtissue. For example, when using three dispensing units, (i) three dispensing units could each include the same bioink, (ii) two dispensing units could include the same bioink and the other dispensing unit could include a different bioink, or (iii) three dispensing units could each include a different bioink.

Having described the components of the bioprinter 10, operation of the bioprinter 10 can be explained further. A microplate including an array of wells (e.g., 384, 1536, or 3456 wells) can be placed on the temperature control plate 50 for receiving bioink 22 that is dispensed from the dispensing unit 12. Alternatively, other cell culture containers without an array of wells (such as a Petri dish or single well plate) on the temperature control plate 50 can directly receive bioink 22 that is dispensed from the dispensing unit 12.

Syringes 14 filled with the same or different bioinks are installed in each dispensing unit 12, and the controller 37 is programmed for a dispensing sequence. The controller 37 places the distal end section 41 of each actuator 38 in contact with the proximal end 18 of the associated plunger 17. The XYZ motion system 80 moves the dispensing units over selected wells (or selected locations on the temperature control plate 50). As the controller drives each actuator 38 toward the plate 50, bioink 22 flows into the fluid path 29 in the nozzle 25. The controllable valve then opens and closes to deliver pulsed fluid (e.g., air) from the source of fluid 34 to the fluid passageway 32 of the fluid port 31. The pulsed fluid creates separate droplets 66 from the flow of bioink in the fluid path 29 in the nozzle 25. A volume of each droplet can be in a range of 10 nanoliters to 15 microliters. The droplets 66 are repeatedly placed on the plate 50 (or in the wells of the microplate) to create the microtissue samples 68 (see FIG. 2). The bioprinter 10 uses volumetric based dispensing, which means the volume of dispensing is linear to the distance that the plunger 17 moves.

The invention is further illustrated in the following Examples which are presented for purposes of illustration and not of limitation.

EXAMPLES

Example 1

Example 1 describes the development of injectable mesenchymal stem cells (MSCs) microtissues for repairing cartilage defects using 3D bioprinting. This is a representative project for our high speed bioprinting in which we bioprint micro-cartilage and bone tissues using human bone marrow mesenchymal stem cells (MSCs). We have successfully bioprinted micro bone tissue and MSC-incorporated-tissue for cartilage and bone regeneration. Our bioprinted micro-tissue is predeveloped and mechanically enhanced in vitro. Once injected in vivo, the tissues self-assemble into large tissue amalgamations which can repair the defects.

Introduction

Articular cartilage exhibits poor intrinsic capacity for repair, and tissue engineering is a new approach for articular cartilage repair. Bone marrow mesenchymal stem cells (MSCs) and bulk hydrogel have been used to repair the cartilage defects in open surgery. As a minimally invasive approach is always preferred for joint surgery, injectable tissue engineered cartilage would be an ideal solution to repair cartilage defects. However, volume shrinkage and poor mechanical properties of hydrogel, which results in void space in the implantation, limit the application of a MSCs-hydrogel injection. In this example, we aimed to develop volume stabilized MSC microtissues using 3D bioprinting, and repair the defect in articular cartilage through the self-assembly of the micro tissues.

Methods 1. 3D bioprinting: The microtissues, comprising human MSCs and bioink composed of hydrogels in the pre-optimized combination, were directly bioprinted using our custom developed 3D bioprinter of the present invention (see FIG. 3).
2. Cell viability: Live/dead cell viability assay in MSC microtissues was performed after bioprinting.
3. Morphology: Morphology of the microtissue was studied by HE staining and confocal microscopy.
4. Dimension alteration: Diameters of the microtissues were imaged by microscopically at a series of time points to analyze the volume alteration.
5. Single tissue 3D out growth: The microtissues were embedded in the hydrogel within a 96-well plate to observe tissue outgrowth under an inverted microscope.
6. Multiple tissue fusion/assembly: MSCs were labeled with Cellbrite (red, green and blue respectively) and several microtissues were placed on the ultra-low attachment surface to observe tissue fusion at different time points.
7. Injectability: The bioprinted microtissues suspended in medium were pushed through a 1.4 mm I.D. needle, and cell viability was analyzed by live/dead staining.
8. Cartilage defect repairing in a cartilage explants culture model: Defects, 2 mm in diameter, were made in the porcine articular cartilage explants. The defects were filled with MSC microtissues to evaluate integration outcome. MSC hydrogel were used as the control. Also, live/dead staining was performed to study cell viability after 2 weeks cultivation.

Results

Figure 3:
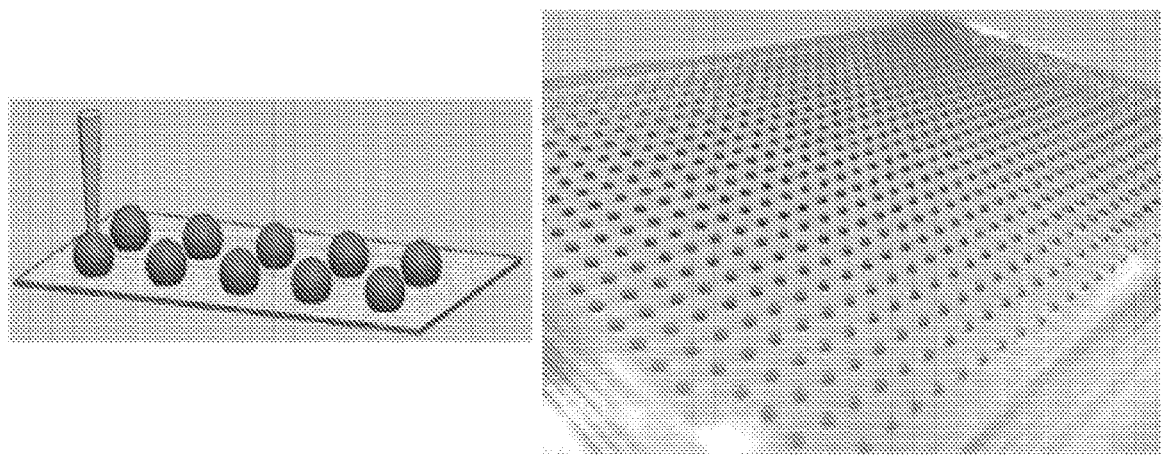
FIG. 3 shows a schematic diagram of one version of a 3D bioprinter of the invention bioprinting mesenchymal stem cell microtissue, and the bioprinted mesenchymal stem cell microtissues.

FIG. 3 shows a schematic diagram of one version of a 3D bioprinter of the invention bioprinting mesenchymal stem cell microtissue, and the bioprinted mesenchymal stem cell microtissues.

Figure 4:
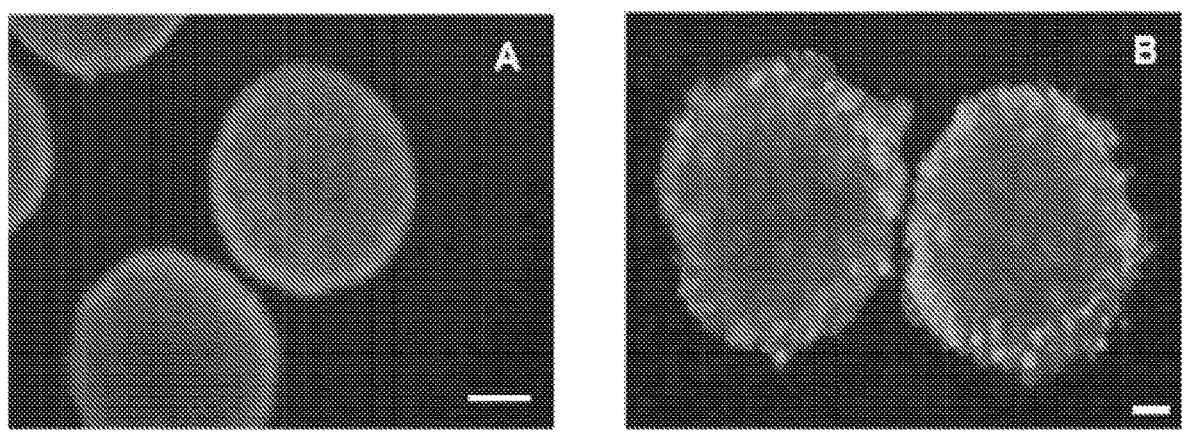
FIG. 4 shows that mesenchymal stem cells (MSCs) in the microtissues exhibit high cell viability after bioprinting (A) and injection through a 1.4 millimeter (mm) inside diameter (I.D.) needle (B). The scale bar is 100 µm.

FIG. 4 shows that mesenchymal stem cells (MSCs) in the microtissues exhibit high cell viability after bioprinting (A) and injection through a 1.4 millimeter (mm) inside diameter (I.D.) needle (B). The scale bar is 100 µm.

Figure 5:
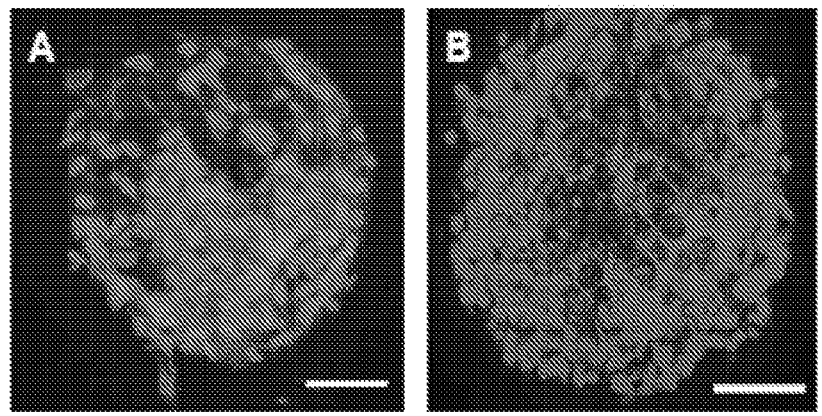
FIG. 5 shows confocal images (A 3D; B section) that revealed the histological architecture of high cell density and extracellular matrix (ECM). The scale bar is 100 µm.

FIG. 5 shows confocal images (A 3D; B section) that revealed the histological architecture of high cell density and ECM. The scale bar is 100 µm.

Figure 6:
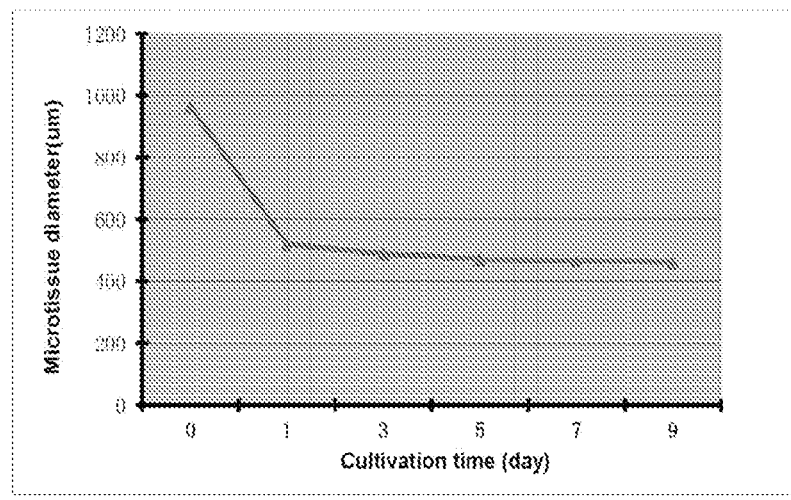
FIG. 6 shows that the dimension of MSC tissues stabilized after 3 days of culture, which is the time point chosen for implantation.

FIG. 6 shows that the dimension of MSC tissues stabilized after 3 days of culture, which is the time point chosen for implantation.

Figure 7:
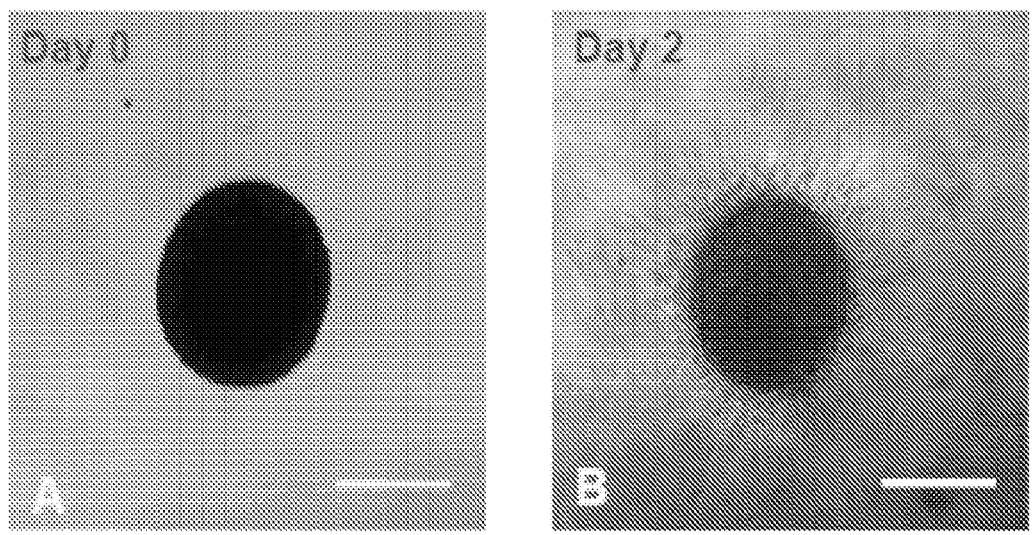
FIG. 7 shows that MSC microtissues out grew into the surrounding hydrogel as shown by phase contrast imaging. The scale bar is 250 µm.

FIG. 7 shows that an MSC microtissue out grew into the surrounding hydrogel as shown by phase contrast imaging. The scale bar is 250 µm.

Figure 8:
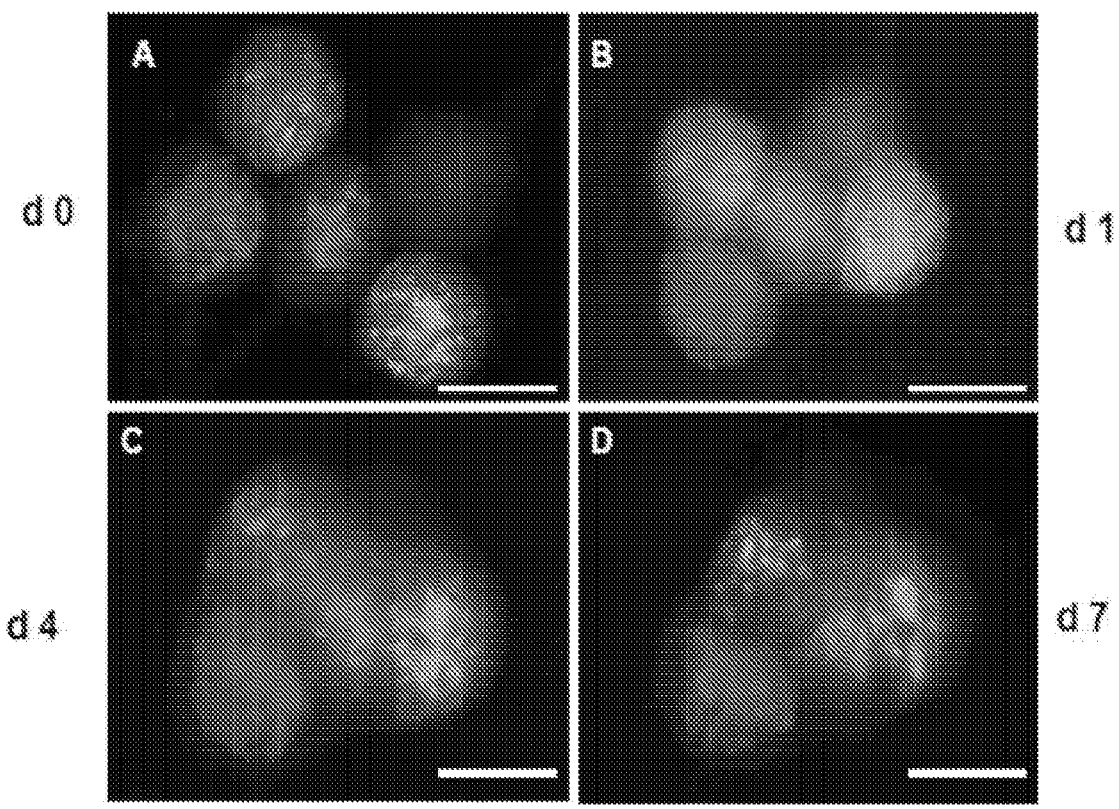
FIG. 8 shows MSCs that were labeled with Cellbrite red, green and blue fluorescent dyes and bioprinted into a individual microtissue respectively. The tissue-fusion was observed when they were placed adjacently. The scale bar is 500 µm.

FIG. 8 shows MSCs that were labeled with Cellbrite red, green and blue fluorescent dyes and bioprinted into a individual microtissue respectively. The tissue-fusion was observed when they were placed adjacently. The scale bar is 500 µm.

Figure 9:
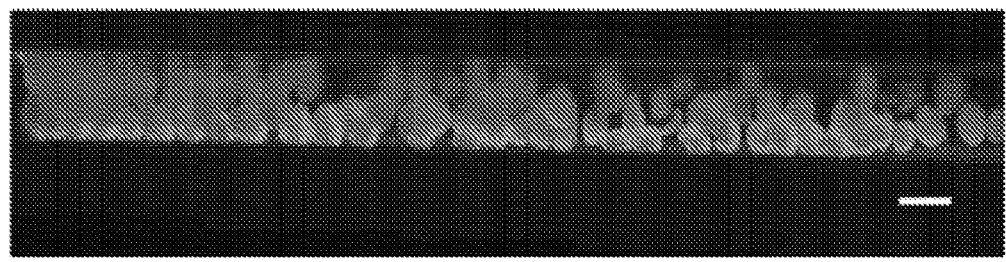
FIG. 9 shows that the printed microtissues could pass through a 1.4 mm I.D. transparent needle. The scale bar is 500 µm. MSCs in the microtissues showed high cell viability after injection as shown in FIG. 4B.

FIG. 9 shows that the printed microtissues could pass through a 1.4 mm I.D. transparent needle. The scale bar is 500 µm. MSCs in the microtissues showed high cell viability after injection as shown in FIG. 4B.

Figure 10:
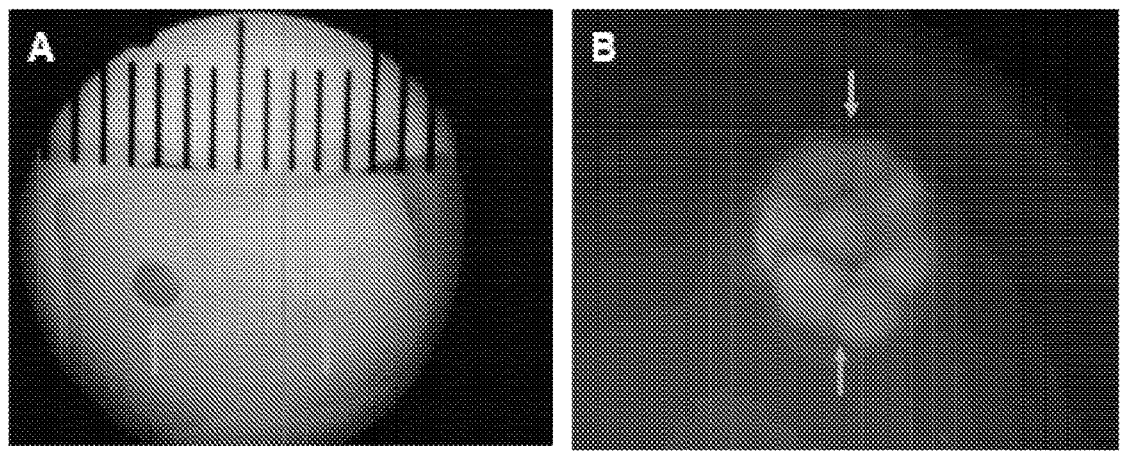
FIG. 10 shows that cartilage defects (2.0 mm, A-left shows the defect) were generated in the porcine articular cartilage explants. Stereo (A-right) and fluorescent microscopic (B) images of the defect show the filling with MSC microtissues.

FIG. 10 shows that cartilage defects (2.0 mm, A-left shows the defect) were generated in the porcine articular cartilage explants. Stereo (A-right) and fluorescent microscopic (B) images of the defect show the filling with MSC microtissues.

Figure 11:
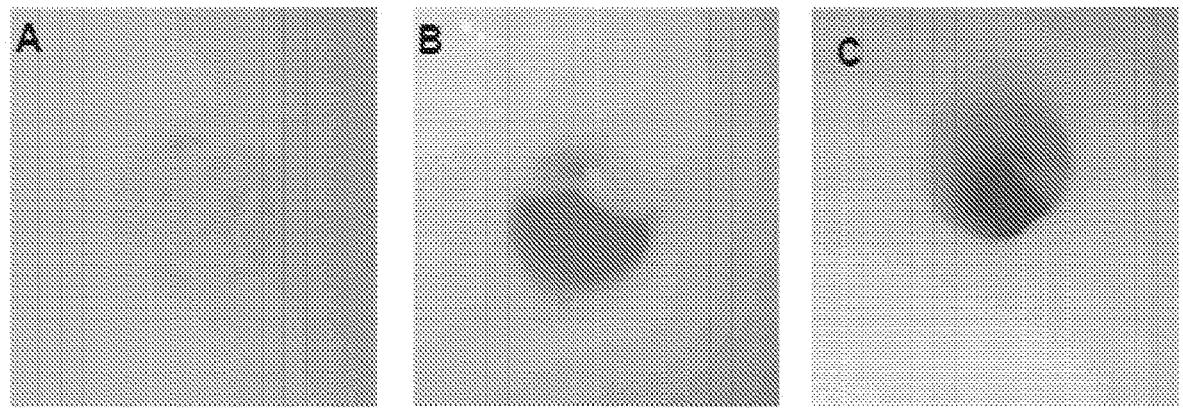
FIG. 11 shows that two weeks after implantation, the defect is still completely filled in the microtissue filled group (A) comparing with large proportion of void space in the MSCs and hydrogel filled group (B) because of gel shrinkage. (C) is the non-treated group.

FIG. 11 shows that two weeks after implantation, the defect is still completely filled in the microtissue filled group (A) comparing with large proportion of void space in the MSCs and hydrogel filled group (B) because of gel shrinkage. (C) is the non-treated group.

Figure 12:
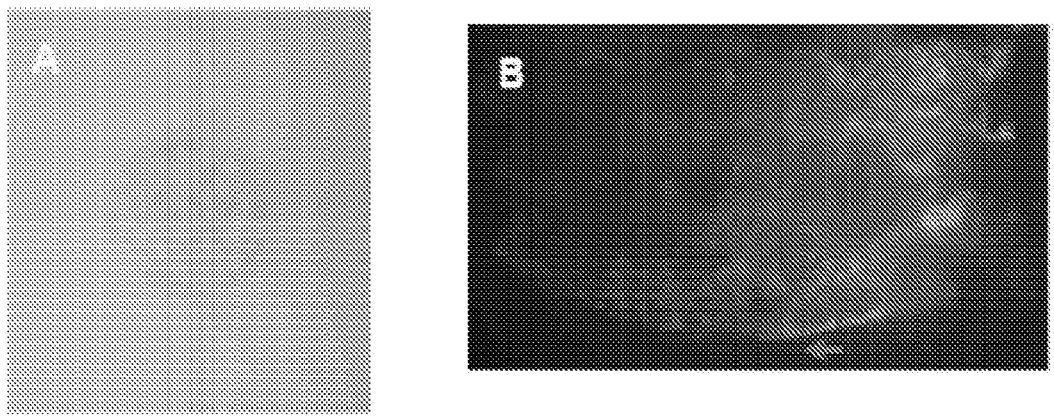
FIG. 12 shows that two weeks after implantation, the explants were sliced perpendicularly along the line as shown in (A). The sliced tissues were stained with cell viability dyes. B is a fluorescent image of section interface (arrow pointing the bottom of the defect). The green fluorescence indicates high cell viability.

FIG. 12 shows that two weeks after implantation, the explants were sliced perpendicularly along the line as shown in (A). The sliced tissues were stained with cell viability dyes. B is a fluorescent image of section interface (arrow pointing the bottom of the defect). The green fluorescence indicates high cell viability.

Conclusion

In Example 1, we have successfully developed a new approach in 3D bioprinting to generate MSC microtissues and it shows promise to repair the articular cartilage defects minimally invasively.

Example 2

Example 2 describes high throughput 3D bioprinting of tumor micro tissues for drug development and personalized cancer therapy.

Introduction

Cancer caused about 25% of all deaths in the United States in 2014. In vitro anti-cancer drug screening is widely used in the pharmaceutical industry and chemosensitivity test for patients. However, only 2D assays and simple 3D culture models were used previously. But these models do not resemble the native tumor microenvironment, or yield inaccurate prediction of drug sensitivity. In this example, we report a novel 3D bioprinted model of tumor microtissues (TMTs), which resemble the native tumor characteristics, for high throughput screening. We characterized the 3D bioprinted tumors in various of aspects.

Figure 13:
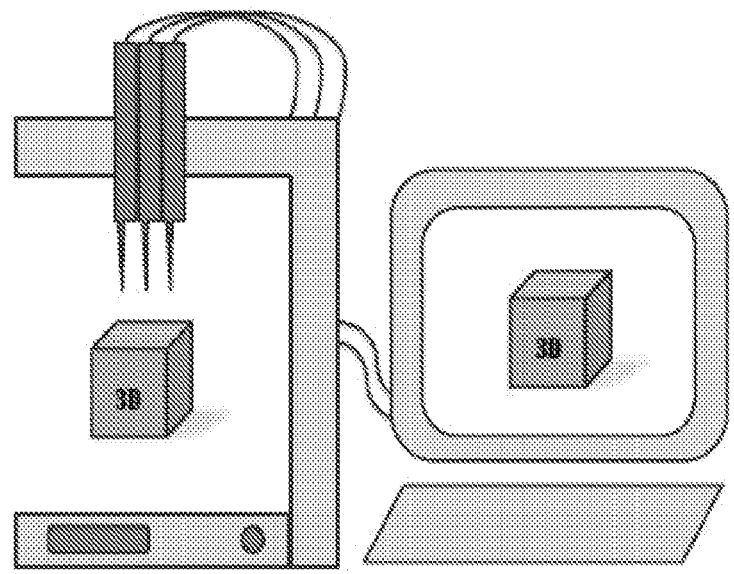
FIG. 13 shows a schematic diagram of a 3D bioprinter of the invention.

Methods 3D bioprinting: The bioink composed of tumor cells, stromal cells and ECM is loaded into our custom developed 3D bioprinter of the present invention. Micro tumor tissues were directly bioprinted into each well of a 96 or 384 well plate. The viability of the cells in the tissues were analyzed using live/dead staining. FIG. 13 shows the schematic diagram of the 3D bioprinter.

Morphologic characterization: The TMTs were cryosectioned or optical sectioned, and analyzed by hematoxylin and eosin (H&E or HE) staining, confocal and multiple-photon microscopy respectively.

Hypoxic micro environment analysis: TMT cryosections were stained by using Hypoxyprobe-Green kit which labels hypoxia area with green fluorescence color.

Invasion assay: The TMTs were first printed and the extra bioink without cells were printed around the tumor tissues. Phase contrast or fluorescent imaging were used to analyze tumor invasion into the matrix.

Angiogenesis assay: In order to analyze the pro-angiogenic biomolecules secreted by tumor tissues. Bioprinted microtissue consisted only Human Umbilical Vein Endothelial Cells (HUVECs) and matrix were imbedded in collagen hydrogel and co-cultured with bioprinted TMT and the angiogenesis sprouting was analyzed by phase contrast and fluorescence microscopy.

Chemosensitivity test: To determine the chemosensitivity of 3D bioprinted TMT and conventional 2D cells, cells and TMTs were plated into each well of a 384-well plate. Drugs were added for 72 hours and live/dead fluorescent was performed. Confocal or multiple-photon microscopy were used to analyze the cell viability in 3D and 2D respectively.

In vivo implantation: Chorioallantoic membrane assay (CAM) was used to evaluate the tumorigenicity in vivo. TMTs were implanted on the top of the growing CAMs on 8th day of development. On the 16th day, each egg was imaged using stereo microscope. The tumors were surgically removed with surrounding membrane and fixed in 4% paraformaldehyde for further histological analysis.

Results

Figure 14:
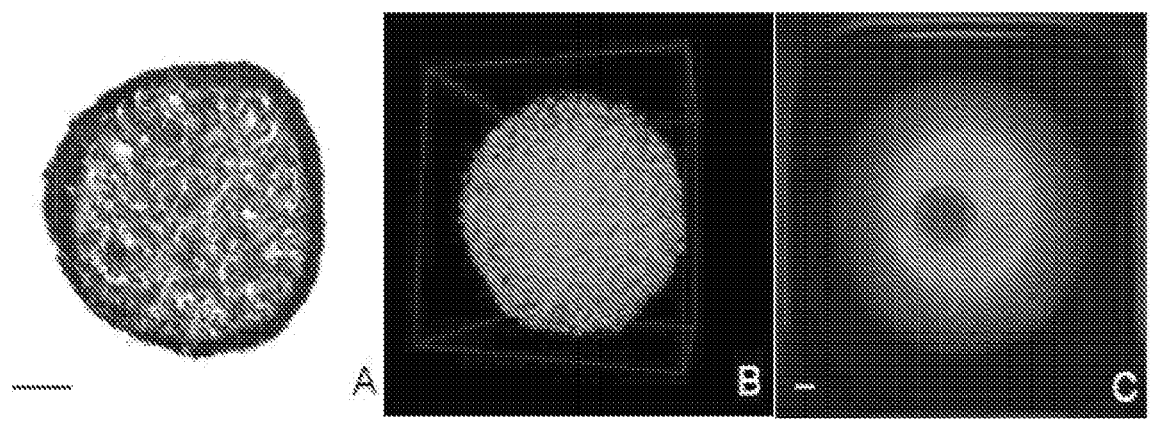
FIG. 14 shows in (A), H&E staining of a bioprinted tumor microtissue (TMT), which has similar morphology to the native tumor tissues. (Bar=100 µm); in (B), 3D volume reconstructed image of a bioprinted TMT, which was imaged by confocal microscopy; and in (C), a representative image of a micro tumor tissue in a well of a 384 well plate, green staining indicates live cells. (Bar=100 µm)

FIG. 14 shows in (A), H&E staining of a bioprinted tumor microtissue (TMT), which has similar morphology to the native tumor tissues. (Bar=100 µm); in (B), 3D volume reconstructed image of a bioprinted TMT, which was imaged by confocal microscopy; and in (C), a representative image of a micro tumor tissue in a well of a 384 well plate, green staining indicates live cells. (Bar=100 µm)

Figure 15:
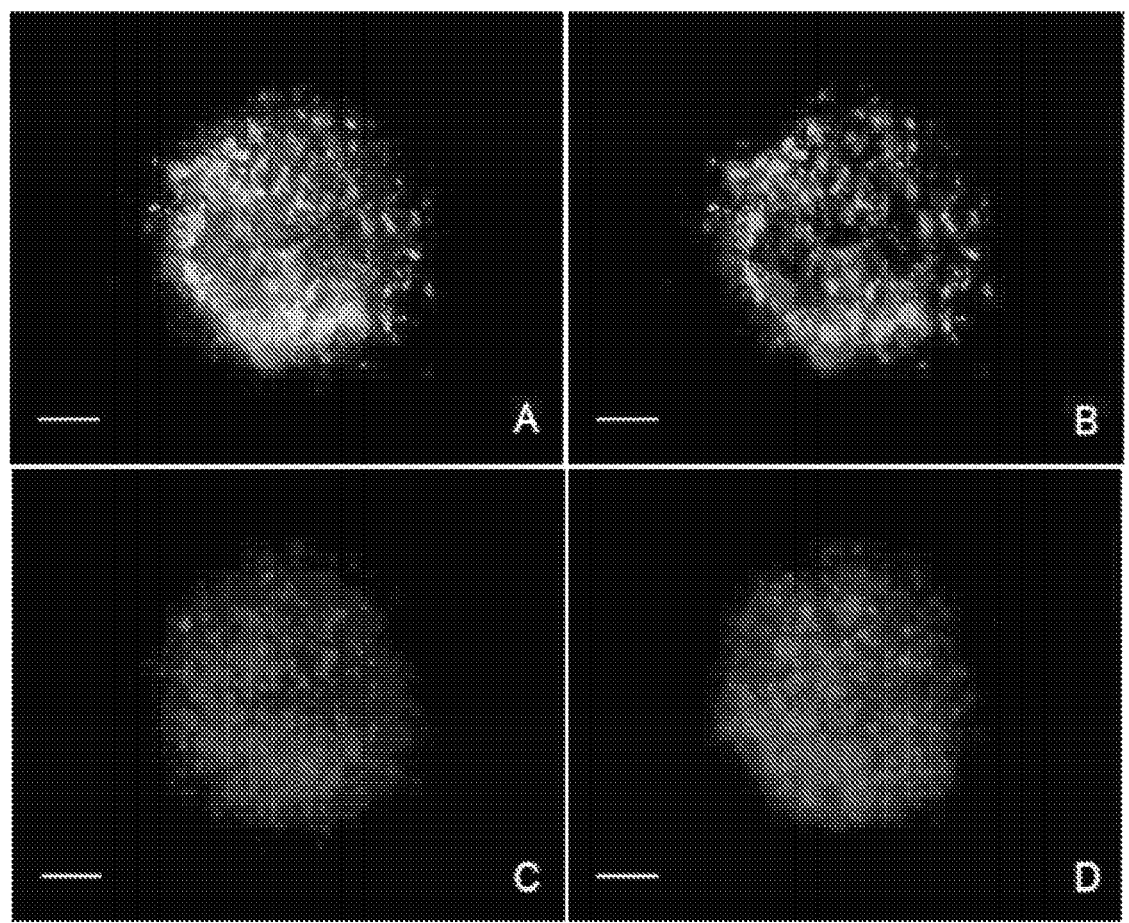
FIG. 15 shows representative images of a TMT in (A), composed of human endothelial cells in (B), human mesenchymal stem cells in (C) and human cancer cells in (D). (Bar=100 µm).

FIG. 15 shows representative images of a TMT in (A), composed of human endothelial cells in (B), human mesenchymal stem cells in (C) and human cancer cells in (D). (Bar=100 µm).

Figure 16:
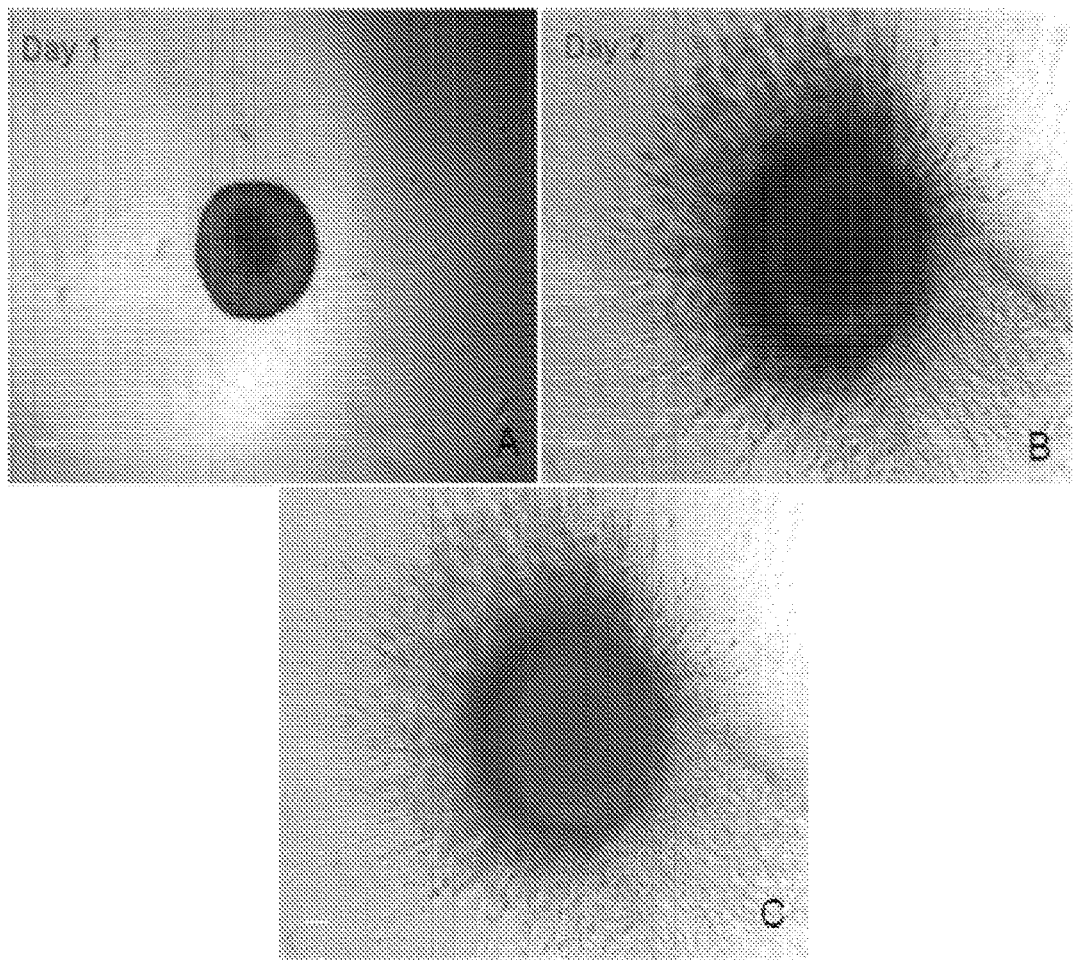
FIG. 16 shows an invasion assay. A TMT invaded into the surrounding matrix after being cultured overnight. The red area (center) in C shows the original location of the TMT at day 1. (Bar=100 µm)

FIG. 16 shows an invasion assay. A TMT invaded into the surrounding matrix after being cultured overnight. The red area (center) in C shows the original location of the TMT at day 1. (Bar=100 µm).

Figure 17:
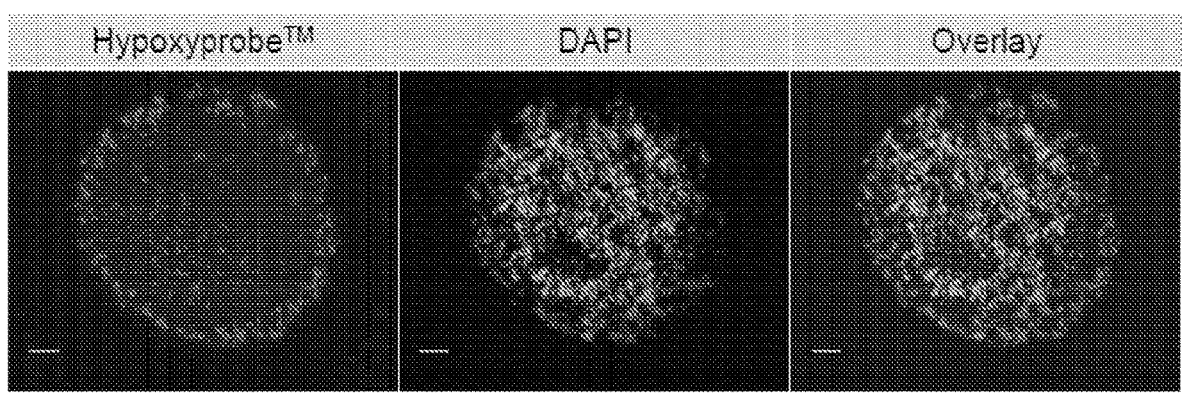
FIG. 17 shows the TMT sections that were stained with a Hypoxyprobe-Green kit which can stain a hypoxia area into a fluorescent green color. A large number of hypoxic cells were observed within the core of the bioprinted micro tumor tissue. (Bar=100 µm)

FIG. 17 shows the TMT sections that were stained with a Hypoxyprobe-Green kit which can stain a hypoxia area into a fluorescent green color. A large number of hypoxic cells were observed within the core of the bioprinted micro tumor tissue. (Bar=100 µm)

Figure 18:
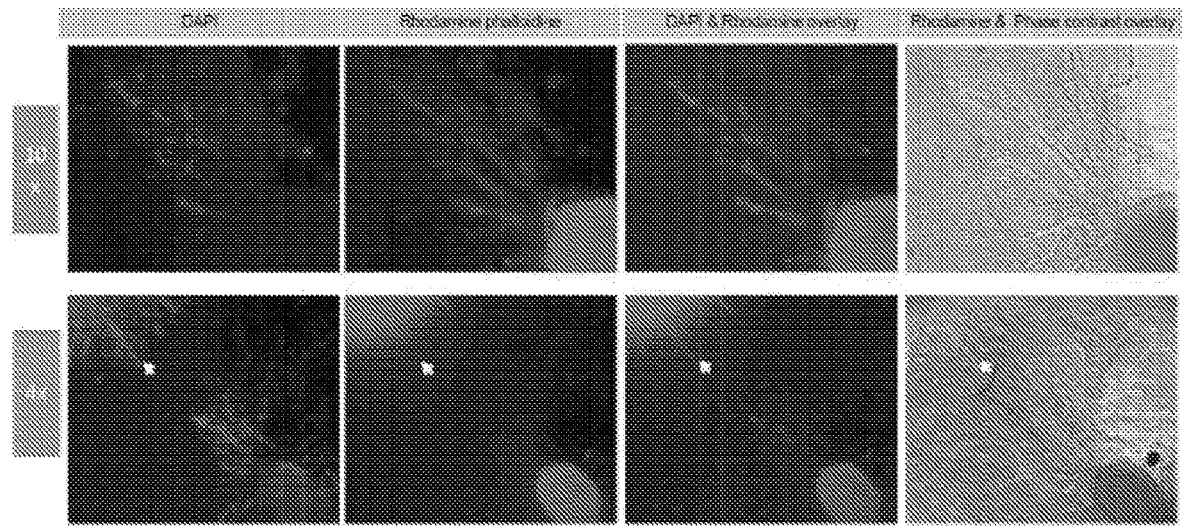
FIG. 18 shows endothelial microtissues that were bioprinted and embedded in the collagen matrix. When co-cultured with a bioprinted tumor microtissue (arrow), a endothelial microtissue robust capillary sprouted. The TMT shows higher pro-angiogenic effect than endothelial microtissue alone or with vascular endothelial growth factor stimulation.

FIG. 18 shows endothelial microtissues that were bioprinted and embedded in the collagen matrix. When co-cultured with a bioprinted tumor microtissue (arrow), an endothelial microtissue robust capillary sprouted. The TMT shows higher pro-angiogenic effect than endothelial microtissue alone or with vascular endothelial growth factor stimulation.

Figure 19:
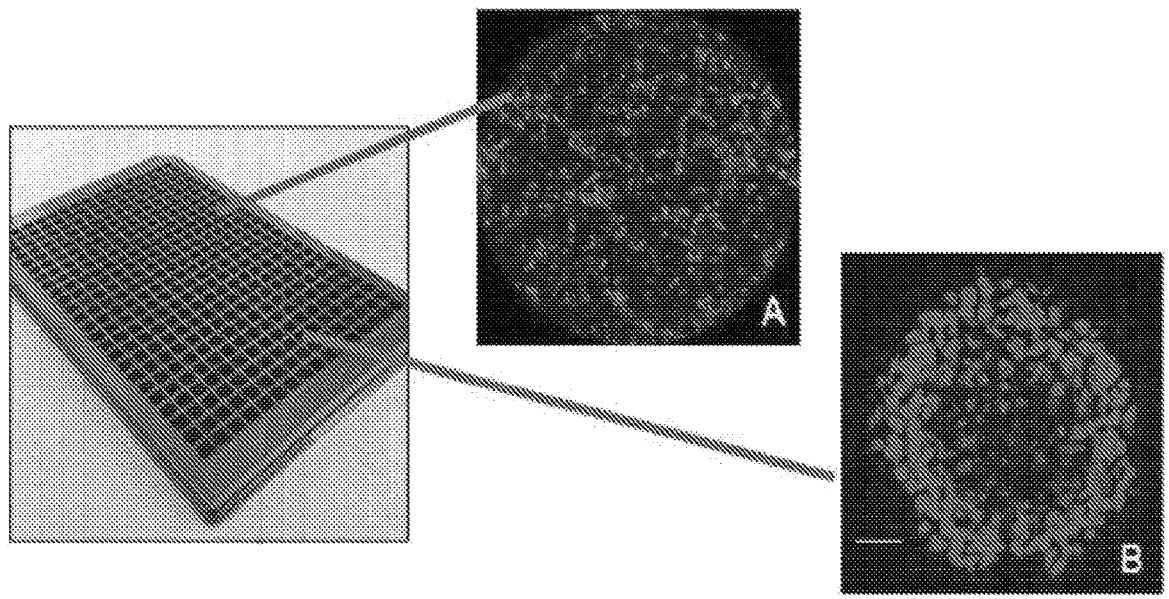
FIG. 19 shows a chemosensitivity analysis using two dimensional tumor cells (A) and TMT (B) in a 384-well plate. After 72 hours of drug treatment, live/dead cell staining with Hoechst dye and propidium iodide (PI) were performed. With confocal or multiple-photon microscopy, optical sections were used for cell viability analysis and to determine the $IC_{50}$. (Bar=50 µm)

FIG. 19 shows a chemosensitivity analysis using two dimensional tumor cells (A) and TMT (B) in a 384-well plate. After 72 hours of drug treatment, live/dead cell staining with Hoechst dye and propidium iodide (PI) were performed. With confocal or multiple-photon microscopy, optical sections were used for cell viability analysis and to determine the $IC_{50}$. (Bar=50 µm)

Figure 20:
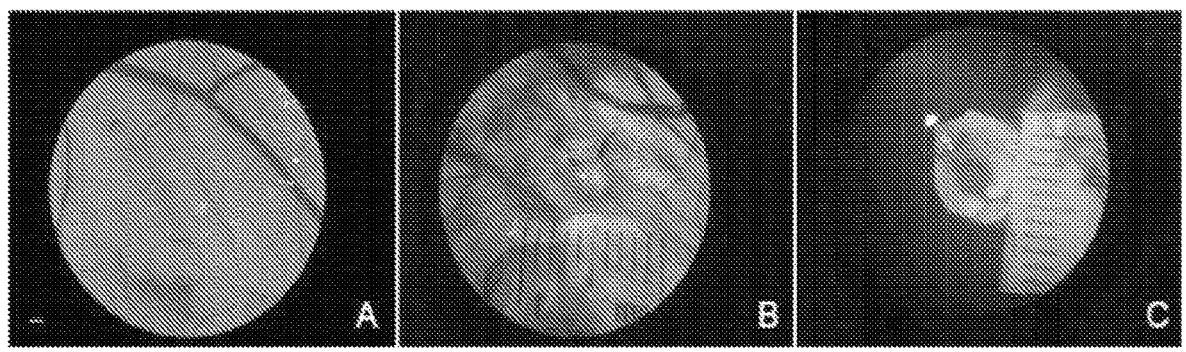
FIG. 20 shows tumor micro tissue implantation that was performed using a CAM model. The stereo microscopic views at the times of (A) implantation (B) 8 days after implantation. In (C), the tumor tissue was surgically removed with surrounding membrane. (Bar=500 µm)

FIG. 20 shows tumor micro tissue implantation that was performed using a CAM model. The stereo microscopic views at the times of (A) implantation (B) 8 days after implantation. In (C), the tumor tissue was surgically removed with surrounding membrane. (Bar=500 µm)

Conclusions

We have successfully developed a high throughput 3D bioprinting system to generate tumor micro tissues in vitro, which resemble many characteristics of the native tumor tissues. The system has therefore demonstrated as a powerful tool for screening anti-cancer drugs and selecting the sensitive drugs for personalized cancer therapy.

Example 3

Figure 21:
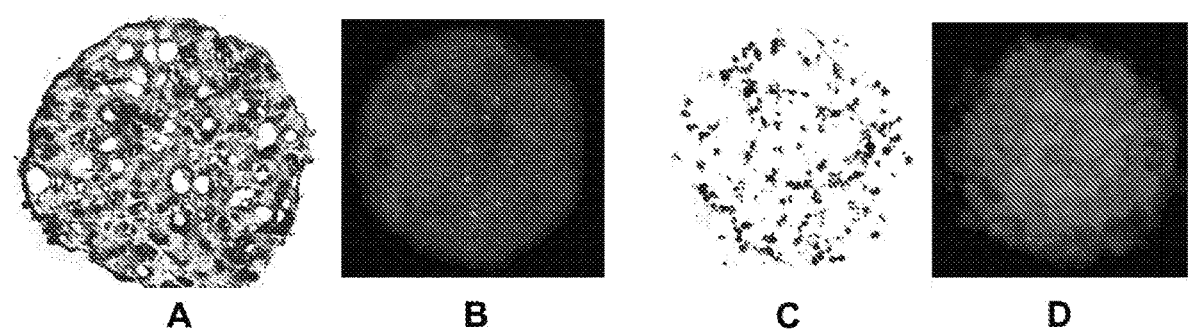
FIG. 21 shows vascularized human micro liver tissues that were bioprinted with HepG2 human liver cells and human endothelial cells. The vascularized micro liver tissues show significant higher cell density (A: H&E staining) and viability (B: live-dead staining, blue indicating live cells and purple indicating dead cells) comparing with non-vascularized micro liver tissues (C: H&E staining. D: live-dead staining).

We 3D bioprinted liver tissues. Specifically, we have successfully bioprinted vascularized human micro liver tissues using HepG2 human liver cells and human endothelial cells. As shown in FIG. 21, the vascularized micro liver tissues show significant higher cell density (A) and viability (B) comparing with non-vascularized micro liver tissues (C and D).

Thus, the invention provides a three dimensional microtissue bioprinter and methods for using the three dimensional microtissue bioprinter. We have disclosed a computer controlled programmable 3D bioprinter for generating live micro tissues with precisely controlled micro-scale accurate XYZ motion and volumetric nanoliter dispensing capability. We have printed many types of tissue with many different types of cells including pluripotent stem cells, bone marrow mesechymal stem cells, osteoblasts, fibroblast, human endothelial cells, liver cells, and many different tumor cells.

We have bioprinted micro tumor tissues for high throughput drug screening and therapeutic purposes. We have characterized many aspects of the printed tumor tissues including morphology, function, biomarker, micro-environment, 3D structure, and invasion and drug sensitivities. As we have experience in tumor bioprinting, we envision successful micro heart and liver tissue printing which requires the same technical procedures with different cells. We 3D bioprinted liver tissues.

We have performed anti-tumor drug screening with 3D bioprinted tumor tissues as described above. This is a desirable service for the pharmaceutical industry to develop new anti-cancer drugs, including but not limited to, chemotherapy drugs, and radiotherapy sensitivity enhancing drugs.

The advantage is that our system can assist in development significantly more quickly and at markedly lower development costs (no animal studies). The 3D nature of the bioprinted tissues should also allow for more accurate assessment compared to currently employed 2D cultured cell screening also saving money and time.

The invention could be used for personalized cancer therapy. Three dimensional bioprinting tumor tissues using cancer cells isolated from individual patients after surgery or biopsy can be used to determine sensitive drug(s) or drug combination(s) for the individual patient, including but not limited to, chemotherapy drugs and radiotherapy-enhancing drugs. Because the 3D tumor tissue closely resembles the in vivo situation, it can more accurately help the oncologists to find the best medication regimen for the patient.

The invention could be used for cartilage and bone tissue regeneration through minimally invasive surgery.

The invention could be used for drug metabolism testing for the pharmaceutical industry. We can utilize our 3D bioprinted micro liver tissues to test drugs under development for their metabolism profiles in high throughput.

The invention could be used for drug toxicity screening for the pharmaceutical industry. We can utilize our 3D bioprinted micro liver and heart tissues to screen for toxicity of candidate drugs for the pharmaceutical industry.

Although the present invention has been described in detail with reference to certain embodiments, one skilled in the art will appreciate that the present invention can be practiced by other than the described embodiments, which have been presented for purposes of illustration and not of limitation. Therefore, the scope of the appended claims should not be limited to the embodiments contained herein.

What is claimed is:

1. A bioprinter comprising:
   one or more dispensing units, each dispensing unit including:
   a syringe including a hollow body and a plunger dimensioned to translate in the body, the body having an exit orifice;
   (ii) an actuator in contact with a proximal end of the plunger;
   (iii) a controller for controlling linear motion of the actuator wherein the controller executes a program received from a computer in the controller to drive the actuator toward the proximal end of the plunger to dispense a bioink from the body of the syringe; and
   (iv) a nozzle having a wall defining a fluid path extending from an inlet of the nozzle to an outlet of the nozzle, the inlet of the nozzle being in fluid communication with the exit orifice of the body of the syringe, wherein as the controller drives the actuator toward the proximal end of the plunger bioink flows into the fluid path,
   wherein the nozzle includes a fluid passageway in fluid communication with a source of fluid and the fluid path,
   wherein the source of fluid comprises a controllable valve for supplying pulsed fluid from the source of fluid to the fluid passageway to create separate droplets from the flow of bioink in the fluid path in the nozzle by blowing the droplets away from the nozzle using the pulsed fluid from the source of fluid.

2. The bioprinter of claim 1 further comprising:
a temperature controller surrounding the body of the syringe.

3. The bioprinter of claim 1 further comprising:
a temperature controlled plate for receiving a bioink from the outlet of the nozzle.

4. The bioprinter of claim 3 further comprising:
a humidifier for creating a humidity controlled zone adjacent to the temperature controlled plate.

5. The bioprinter of claim 1 wherein:
a volume of each droplet is in a range of 10 nanoliters to 15 microliters.

6. The bioprinter of claim 1 wherein:
the controllable valve is controlled by a second controller.

7. The bioprinter of claim 1 wherein:
the pulsed fluid comprises pulsed air.

8. The bioprinter of claim 1 wherein:
the pulsed fluid comprises millisecond pulsed air.

9. The bioprinter of claim 1 wherein:
each dispensing unit is a non-contact dispensing unit.

10. The bioprinter of claim 1 wherein:
the nozzle is integral with the syringe body.

11. The bioprinter of claim 1 wherein:
the nozzle is separate from the syringe body.

12. The bioprinter of claim 1 wherein:
the outlet of the nozzle has an inner diameter of 100 microns to 3 millimeters.

13. The bioprinter of claim 1 wherein:
the bioprinter comprises a plurality of the dispensing units.

14. The bioprinter of claim 1 further comprising:
each of the dispensing units is mounted on an XYZ motion system.

* * * * *

UNITED STATES PATENT AND TRADEMARK OFFICE
CERTIFICATE OF CORRECTION

PATENT NO. : 11,400,183 B2
APPLICATION NO. : 15/757461
DATED : August 2, 2022
INVENTOR(S) : Yonggang Pang et al.

It is certified that error appears in the above-identified patent and that said Letters Patent is hereby corrected as shown below:

In the Specification

Column 13, Claim 1, Line 37, "a syringe" should be --(i) a syringe--.

Signed and Sealed this
Eighth Day of November, 2022

Katherine Kelly Vidal
*Director of the United States Patent and Trademark Office*